(12) United States Patent
Iinuma et al.

(10) Patent No.: US 7,387,800 B2
(45) Date of Patent: Jun. 17, 2008

(54) SESQUITERPENOID DERIVATIVES HAVING ADIPOCYTE DIFFERENTIATION INHIBITORY EFFECT

(75) Inventors: Munekazu Iinuma, Gifu (JP); Toshiyuki Tanaka, Gifu (JP); Makoto Ubukata, Hokkaido (JP); Nobuyasu Matsuura, Okayama (JP); Masashi Yamada, Tokyo (JP); Hiroto Suzuki, Toyama (JP)

(73) Assignee: Meiji Dairies Corporation, Tokyo (JP)

( * ) Notice: Subject to any disclaimer, the term of this patent is extended or adjusted under 35 U.S.C. 154(b) by 316 days.

(21) Appl. No.: 10/485,801

(22) PCT Filed: Aug. 9, 2002

(86) PCT No.: PCT/JP02/08178

§ 371 (c)(1),
(2), (4) Date: Sep. 13, 2004

(87) PCT Pub. No.: WO03/015765

PCT Pub. Date: Feb. 27, 2003

(65) Prior Publication Data

US 2005/0048135 A1 Mar. 3, 2005

(30) Foreign Application Priority Data

Aug. 15, 2001 (JP) ............................. 2001-246777

(51) Int. Cl.
*A61K 36/00* (2006.01)
(52) U.S. Cl. ...................................... 424/725; 514/175
(58) Field of Classification Search ..................... None
See application file for complete search history.

(56) References Cited

OTHER PUBLICATIONS

Heinrich (Phytotherapy Reasearch (2000), vol. 14, pp. 479-488).*
http://www.obesity.org/prevention/preventing.shtm—accessed 4/9/07.*
http://www.surgeongeneral.gov/topics/obesity/calltoaction/fact_vision.htm—accessed Apr. 9, 2007.*
Caplus abstract of Borges del Castillo et al. (Rev. Latinoam Quim. (1984), vol. 15, No. 3-4, pp. 96-106).*
Registry entry for RN 95349-42-1.*
English translation for Borges del Castillo et al. (Rev. Latinoam Quim. (1984), vol. 15, No. 3-4, pp. 96-106).*
Registry entry of 95349-43-2.*
Ramos et al. (1992) Medline Accession No. NLM 308793.*
Borges del Castillo, J. et al. (1984) "Locatonas Sesquiterpenicas Del Genero Calea: Caleinolidos, Un Tipo Especial De Heliangolidos" *Rev. Latinoam Quim* 15(3-4):-96-106.
Hall, I.H. et al. (Jun. 1980) "Antihyperlipidemic Activity of Sesquiterpene Lactones and Related Compounds" *Journal of Pharmaceutical Sciences* 69(6):694-697.
Herz, Werner and Narendra Kumar (1980) "Sesquiterpene Lactones of *Calea zacatechichi* and *C. urticifolia*" *Phytochemistry* 19:593-597.
Sweet Valley, Discovery of Substances from Plants that are Effective in the Treatment and Prevention of Cancer and Obesity (Nov. 2001) 'Online! http://www.sweetvalley.jp/j/news/news000026.htn.
Ramos, Ruben Roman et al. (1992) "Hypoglycemic Effect of Plants Used in Mexico as Antidiabetics" *Archives of Medical Research* 23(1):59-64.
Borges del Castillo, Jr. et al. (1984) STN Accession No. 102:182384.

* cited by examiner

*Primary Examiner*—Susan Coe Hoffman
(74) *Attorney, Agent, or Firm*—Saliwanchik, Lloyd & Saliwanchik

(57) ABSTRACT

The objective of the present invention is to identify compounds having an inhibitory effect on adipocyte differentiation, and to provide pharmaceutical compositions and food compositions for prevention, improvement, or treatment of obesity or obesity related diseases. By enthusiastically studying natural products that inhibit the differentiation induction of adipocyte precursors into adipocytes, sesquiterpenoid derivatives, which are extracts from a Compositae plant, Calea, growing in Central and South America, were demonstrated to have an excellent inhibitory effect on adipocyte differentiation induction. Calea extract or the sesquiterpenoid derivatives are expected to be used in pharmaceutical compositions and food compositions for prevention, improvement, or treatment of obesity related diseases.

4 Claims, 4 Drawing Sheets

SESQUITERPENOID DERIVATIVES HAVING ADIPOCYTE DIFFERENTIATION INHIBITORY EFFECT

This application is a National Stage Application of International Application Number PCT/JP02/08178, published, pursuant to PCT Article 21(2); which claims priority to Japanese Application 2001-246777, filed Aug. 15, 2001.

TECHNICAL FIELD

The present invention relates to adipocyte differentiation inhibitors containing sesquiterpenoid derivatives that have an inhibitory effect on adipocyte differentiation as active ingredients, and pharmaceutical compositions and food compositions for prevention, improvement, or treatment of diseases caused by the induction of adipocyte differentiation.

BACKGROUND ART

Obesity is caused by overeating, lack of exercise, abnormal feeding pattern, genetic predisposition, thermogenesis impairment, and such. Excess energy resulting from imbalance of intake and expenditure of energy is stored in adipocytes, and these adipocytes gather to form adipose tissue. That is, obesity is a condition of hyperplasia of adipose tissues.

In addition, obesity is thought to be a major risk factor for heart diseases (angina pectoris, myocardial infarction, cardiac hypertrophy, heart failure, etc.), vascular disorders (hypertension, arteriosclerosis, cerebral thrombosis, cerebral infarction, etc.) diabetes, gout, hyperlipemia, fatty liver, gallstone, pancreatitis, osteoarthritis, hernia, and such.

Adipocytes are produced from mesenchymal cells and are formed by differentiation induction from adipocyte precursors. Therefore, adipocyte formation can be suppressed by inhibiting differentiation induction of adipocyte precursors to form adipocytes. When the formation of adipocyte is suppressed, adipose tissue will not be formed. Thus, compounds that inhibit differentiation of adipocytes are considered to have preventive or therapeutic effects against obesity related diseases.

DISCLOSURE OF THE INVENTION

An objective of the present invention is to identify compounds having inhibitory effects on adipocyte differentiation, and to provide pharmaceutical compositions and food compositions for prevention, improvement, or treatment of obesity or obesity related diseases.

In order to achieve the above-mentioned objective, the present inventors made every effort to study natural products that inhibit the differentiation induction of adipocyte precursors to adipocytes. As a result, sesquiterpenoid derivatives extracted from a Compositae plant, *Calea,* growing in Central and South America, were found for the first time to possess an excellent inhibitory effect on the induction of adipocyte differentiation. Therefore, there is a great expectation that these sesquiterpenoid derivatives may be used in pharmaceutical compositions and food compositions for prevention, improvement, or treatment of obesity or obesity related diseases.

More specifically, the present invention relates to an adipocyte differentiation inhibitor containing a sesquiterpenoid derivative that has an inhibitory effect on adipocyte differentiation as an active ingredient, and also to pharmaceutical compositions and food compositions for prevention, improvement, or treatment of obesity or obesity related diseases, and more specifically provides:

[1] a *Calea* extract having an inhibitory effect on adipocyte differentiation;

[2] the *Calea* extract according to [1], wherein said *Calea* is selected from the group consisting of *Calea urticifolia, Calea pinnatifida, Calea uniflora, Calea axillaris, Calea insignis, Calea integrifolia, Calea nelsonii, Calea peduncularis, Calea pringlei, Calea purpusii, Calea sabazioides, Calea savannarum, Calea scabra, Calea sororia, Calea standleyi, Calea tejadae,* and *Calea zacatechichi;*

[3] a sesquiterpenoid derivative having an inhibitory effect on adipocyte differentiation;

[4] a sesquiterpenoid derivative of any one of structural formula (1) to (4):

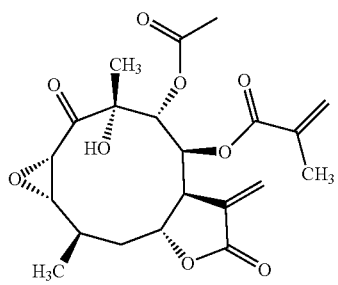

(1) compound 1

$C_{21}H_{26}O_9$
Exact Mass: 422.16
Mol. Wt.: 422.43
C, 59.71; H, 6.20; O, 34.09

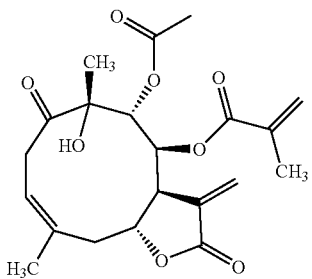

(2) compound 4

$C_{21}H_{26}O_8$
Exact Mass: 406.16
Mol. Wt.: 406.43
C, 62.06; H, 6.45; O, 31.49

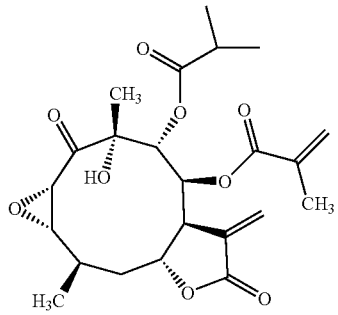

(3) compound 7

$C_{23}H_{30}O_9$
Exact Mass: 450.19
Mol. Wt.: 450.48
C, 61.32; H, 6.71; O, 31.96

-continued (4) compound 12

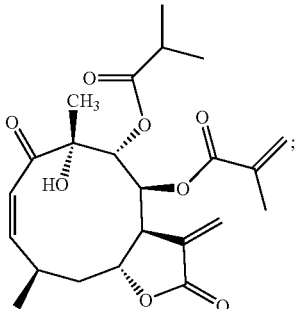

C₂₃H₃₀O₈
Exact Mass: 434.19
Mol. Wt.: 434.48
C, 63.58; H, 6.96; O, 29.46

[5] a sesquiterpenoid derivative having an inhibitory effect on adipocyte differentiation of any one of structural formula (1) to (4) of [4] and (5) to (7):

(5) compound 3

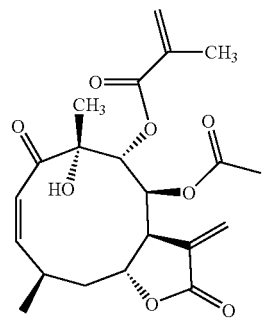

C₂₁H₂₆O₈
Exact Mass: 406.16
Mol. Wt.: 406.43
C, 62.06; H, 6.45; O, 31.49

(6) compound 6

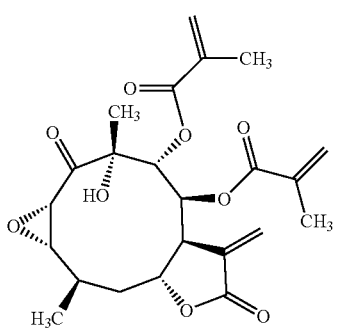

C₂₃H₂₈O₉
Exact Mass: 448.17
Mol. Wt.: 448.46
C, 61.60; H, 6.29; O, 32.11

-continued (7) compound 11

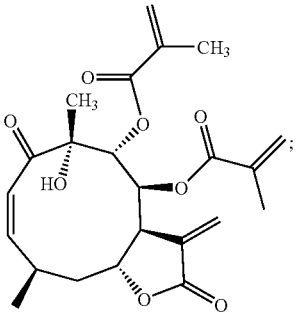

C₂₃H₂₈O₈
Exact Mass: 432.18
Mol. Wt.: 432.46
C, 63.88; H, 6.53; O, 29.60

[6] an adipocyte differentiation inhibitor containing the *Calea* extract according to [1] or [2], or the sesquiterpenoid derivative according to [3] or [5] as an active ingredient;

[7] a pharmaceutical composition for prevention, improvement, or treatment of obesity or obesity related diseases, containing the *Calea* extract according to [1] or [2], or the sesquiterpenoid derivative according to [3] or [5] as an active ingredient;

[8] the pharmaceutical composition according to [7], wherein the disease is selected from the group consisting of heart disease, vascular disorder, diabetes, gout, hyperlipemia, fatty liver, gallstone, pancreatitis, osteoarthritis, and hernia; and

[9] a food composition for prevention or improvement of obesity or obesity related diseases, containing the *Calea* extract according to [1] or [2], or the sesquiterpenoid derivative according to [3] or [5] as an active ingredient.

The present inventors discovered that the *Calea* plant extract, sesquiterpenoid derivatives, have an inhibitory effect on the induction of adipocyte differentiation. Therefore, the present invention provides *Calea* extract having adipocyte differentiation inhibitory effect.

*Calea* is a plant belonging to Compositae and grows mainly in Central and South America. The *Calea* of the present invention includes *Calea urticifolia, Calea pinnatifida, Calea uniflora, Calea axillaris, Calea insignis, Calea integrifolia, Calea nelsonii, Calea peduncularis, Calea pringlei, Calea purpusii, Calea sabazioides, Calea savannarum, Calea scabra, Calea sororia, Calea standleyi, Calea tejadae*, and *Calea zacatechichi*, but is not particularly limited to these species or variations.

The term "*Calea* extract" herein refers to a substance extracted from all or a portion of the *Calea* plant. The *Calea* extract of the present invention is typically in a liquid form (for example, *Calea* extract solution) but is not limited thereto, and includes also powdered substances made upon drying the extracted solution, or substance obtained by cutting or grinding an arbitrary portion of *Calea*. The *Calea* extract of the present invention can be obtained by extracting all or an arbitrary portion of the *Calea* plant. However, extract from the entire plant is especially preferable.

The *Calea* extract of the present invention can be obtained according to the method for preparing plant extract solutions generally performed by those skilled in the art. For example, the Calea extract solution can be obtained according to the following method. First, the collected plant is cut and is dried in a cool place away from direct sunlight. Then, following the production of powder using a grinder, a variety of appropriate organic solvents, water, or their mixed solutions are used for extraction by heated reflux. Next, the extracted solution is filtered, and concentrated under reduced pressure to obtain a concentrated extract.

Whether the *Calea* extract obtained by the above-mentioned method has an inhibitory effect on adipocyte differentiation or not can be evaluated, for example, by measuring acetic acid ($^{14}C$—$CH_3COOH$) incorporation activity, or by glucose ($^{14}C$-2-deoxyglucose) incorporation activity described later in the Examples. Examples of biochemical evaluation methods include measurements of glucose-6-phosphate dehydrogenase activity, neutral fat releasing activity, and such. In addition, regarding detection at the mRNA level, evaluation can be conducted by detecting adipocyte differentiation markers, such as the aP2 gene.

Furthermore, the present inventors discovered that sesquiterpenoid derivatives contained in *Calea* extract have an inhibitory effect on adipocyte differentiation. Therefore, the present invention provides sesquiterpenoid derivatives having adipocyte differentiation inhibitory effect.

The sesquiterpenoid derivative of the present invention having adipocyte differentiation inhibitory effect may be a natural compound (for example, a compound extracted from plants other than *Calea*) or an artificially synthesized compound.

Compounds having the characteristics (chemical formula, structural formula, molecular weight, etc.) indicated in the following (1) to (7) may be cited as examples of the sesquiterpenoid derivatives of the present invention having adipocyte differentiation inhibitory effects.

-continued

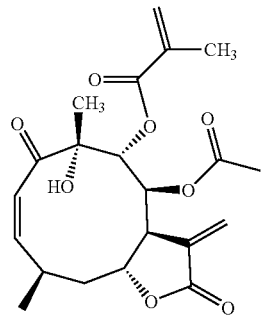

(2) compound 3

$C_{21}H_{26}O_8$
Exact Mass: 406.16
Mol. Wt.: 406.43
C, 62.06; H, 6.45; O, 31.49

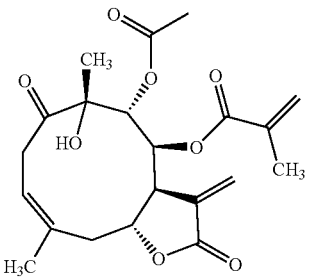

(3) compound 4

$C_{21}H_{26}O_8$
Exact Mass: 406.16
Mol. Wt.: 406.43
C, 62.06; H, 6.45; O, 31.49

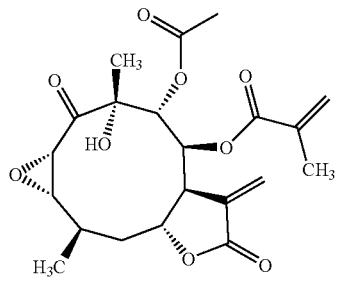

(1) compound 1

$C_{21}H_{26}O_9$
Exact Mass: 422.16
Mol. Wt.: 422.43
C, 59.71; H, 6.20; O, 34.09

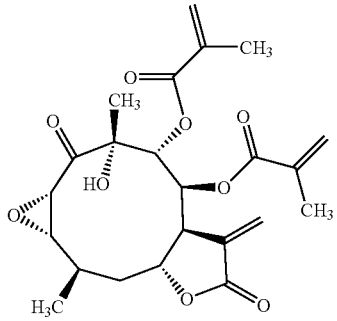

(4) compound 6

$C_{23}H_{28}O_9$
Exact Mass: 448.17
Mol. Wt.: 448.46
C, 61.60; H, 6.29; O, 32.11

-continued (5) compound 7

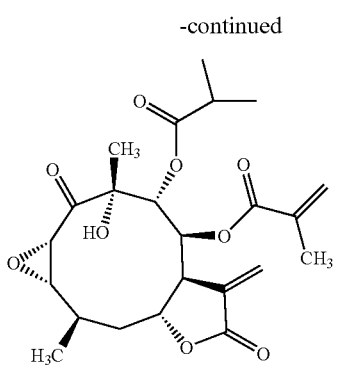

C$_{23}$H$_{30}$O$_9$
Exact Mass: 450.19
Mol. Wt.: 450.48
C, 61.32; H, 6.71; O, 31.96

(6) compound 11

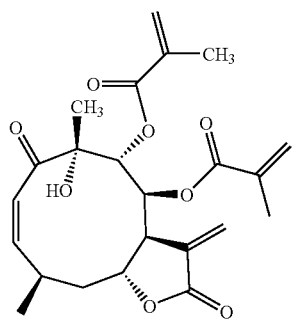

C$_{23}$H$_{28}$O$_8$
Exact Mass: 432.18
Mol. Wt.: 432.46
C, 63.88; H, 6.53; O, 29.60

(7) compound 12

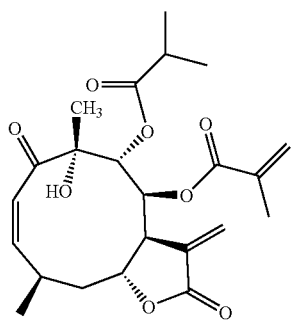

C$_{23}$H$_{30}$O$_8$
Exact Mass: 434.19
Mol. Wt.: 434.48
C, 63.58; H, 6.96; O, 29.46

The above-mentioned compounds 1, 4, 7, and 12 are compounds found for the first time in the present invention. The present invention also provides these novel compounds. Furthermore, the sesquiterpenoid derivative of the present invention includes analogs of the above-mentioned compounds, or compounds produced as derivatives based on these compounds so long as they possess an inhibitory effect on adipocyte differentiation. For example, a compound wherein a functional group of the above-mentioned compound is replaced with another functional group is included in the compound of the present invention so long as it has an inhibitory effect on adipocyte differentiation. Furthermore, some compounds are known to become pro-drugs (a drug that shows activity only after being metabolized in vivo due to modification of the chemical structure) by esterification. Such chemically modified sesquiterpenoid derivatives (such as pro-drug, etc.) are also included in the present invention.

In addition, the present invention provides *Calea* extract having adipocyte differentiation inhibitory effect, or adipocyte differentiation inhibitor containing sesquiterpenoid derivatives as the active ingredient. Adipocytes are produced from mesenchymal cells and are formed by differentiation induction from adipocyte precursors. Compounds having an inhibitory effect on adipocyte differentiation suppress the formation of adipocytes, and as a result, adipose tissue formation is expected to be suppressed. Therefore, such compounds are expected to be not only useful as reagents for suppressing adipocyte differentiation, but also effective in prevention, improvement, or treatment of obesity or obesity related diseases. Thus, the present invention provides *Calea* extract, or pharmaceutical compositions containing sesquiterpenoid derivatives as the active ingredient for prevention, improvement, or treatment of obesity or obesity related diseases.

The term "prevention" herein includes not only prevention before having the disease, but also prevention against recurrence of the disease after treatment. Specifically, "obesity related diseases" that are the targets of prevention, improvement, or treatment of the present invention include, for example, heart diseases (angina pectoris, myocardial infarction, cardiac hypertrophy, heart failure, etc.), vascular disorders (hypertension, arteriosclerosis, cerebral thrombosis, cerebral infarction, etc.), diabetes, gout, hyperlipemia, fatty liver, gallstone, pancreatitis, osteoarthritis, hernia, and such, but are not particularly limited to these diseases.

When using the adipocyte differentiation inhibitor, the anti-obesity drug for prevention, improvement, or treatment of obesity, and the pharmaceutical compositions for prevention, improvement, or treatment of obesity related diseases of the present invention, it is prepared as a generic medical formulation. For example, the medicament of the present invention is prescribed in a form suited for oral administration or parenteral administration as a formulation, such as pharmaceutical compositions or tablet, pill, powder, granule, encapsulated formulation, troche, syrup, solution, emulsion, suspension, injection obtained by mixing with carriers (excipient, binder, disintegrant, corrigent for taste, corrigent for smell, emulsifier, diluent, adjuvant, etc.) acceptable for formulation.

Examples of excipient include lactose, cornstarch, white sugar, glucose, sorbitol, plasma cellulose, and such. Examples of binders include polyvinyl gum arabia, tragacanth, gelatin, shellac, hydroxypropylcellulose, hydroxypropyl starch, polyvinylpyrrolidone, and such.

Examples of disintegrants include starch, agar, gelatin powder, crystalline cellulose, calcium carbonate, sodium bicarbonate, calcium citrate, dextran, pectin, and such. Examples of lubricants are magnesium stearate, talc, polyethylene glycol, silica, hardened vegetable oil, and such. Further, coloring agents acceptable for addition into medicaments may be used. Example of corrigents for taste and smell include cocoa powder, 1-menthol, aromatic acids, peppermint oil, Borneo camphor, cinnamon powder, and such. These tablets and granules may be appropriately coated as necessary with sugar coating, gelatin coating, and so on.

When preparing an injection, pH regulator, buffer, stabilizer, preservative, and such, are added as necessary, and is made into a subcutaneous, intramuscular, or intravenous injection by conventional methods. The injection can be a formulation that is prepared just before use by storing the solution into a container, then producing a solid formulation by freeze drying and such. A single dose can be stored into a container, and a dose can be stored into the same container.

The dosage of the adipocyte differentiation inhibitor, the anti-obesity drug for prevention, improvement, or treatment of obesity, and the pharmaceutical composition for prevention, improvement, or treatment of obesity related diseases of the present invention is determined by considering the type of dosage form, administration method, age and weight of the subject (mammals including humans), condition of the subject, and such. Specifically, for an adult patient, for example, 0.01 to 600 mg can be administered orally per day as 1 to several doses. Examples of doses are more preferably 0.1 to 400 mg/day, and even more preferably 1 to 200 mg/day. Although these doses vary depending on the weight and age of the patient, and on the administration method, one skilled in the art can appropriately select the correct dose. It is also preferable to appropriately determine the administration period depending on the healing course of the patient, and such.

A preferred embodiment of the above-mentioned pharmaceutical composition of the present invention may be an oral composition. Specifically, the oral composition may be, for example, in a dry powdered form of the *Calea* extract of the present invention. The dry powder may be prepared, for example, according to the method selected from (a) and (b) mentioned below:

(a) freeze-drying method: The extract solution is suspended in water, and frozen. Then, the frozen solution is dried by subliming water by reduced pressure to powderize the extract solution; and (b) spray-drying method: The extract solution or suspension is sprayed into hot air and is dried instantaneously to obtain a spherical dried substance.

In addition, the present invention provides food compositions for prevention or improvement of obesity or obesity related diseases that contain *Calea* extract, or sesquiterpenoid derivatives as active ingredients. Examples of the food compositions of the present invention are health food, functional food, specified health food, nutritional supplements, enteral nutrition, and such, but are not limited to these foods as long as it has the effect of preventing or improving obesity or obesity related diseases. The food compositions of the present invention may be used favorably in the form of the above-mentioned oral composition. Further, the present invention includes the use of the dried powder or the extract for producing oral compositions for improvement, or prevention, or otherwise prevention of recurrence of diseases caused by adipocyte differentiation induction in mammals, including humans. The production method of the oral compositions is a well known, frequently used technology for those skilled in the art. More specifically, the sesquiterpenoid derivative of the present invention or *Calea* extract solution or dried *Calea* powder containing the sesquiterpenoid derivative can be processed into health food, functional food, specified health food, nutritional supplements, enteral nutrition, and such, by mixing compositions that are acceptable in terms of food sanitation. For example, compositions, such as stabilizers, preservatives, coloring agents, fragrances, and vitamins, can be added appropriately to the above-mentioned sesquiterpenoid derivatives, or to the *Calea* extract solution and dried *Calea* powder containing the sesquiterpenoid derivatives, mixed, and then formed appropriately by conventional methods for oral compositions, such as tablet, particulate, granule, powder, capsule, liquid, cream, beverage, and such.

Any patents, patent applications, and publications cited herein are incorporated by reference.

BEST MODE FOR CARRYING OUT THE INVENTION

Hereinafter, the present invention will be described more specifically by way of Examples, but the present invention is not limited to these Examples.

EXAMPLE 1

Evaluation of the Inhibitory Effect of *Calea* Extract Solution on Adipocyte Differentiation Induction Whether *Calea* extract solution has an inhibitory activity on adipocyte differentiation induced by the addition of insulin was investigated. First, the aerial portion of *Calea* (170 g) was ground, and extracted by heated reflux using acetone (24 hours×2 times) to produce *Calea* extract solution. The extracted solution was filtered, and then concentrated under reduced pressure to yield a concentrated extract. Mouse adipocyte precursors (3T3-L1) obtained from Human Science Research Resources Bank was used as the adipocyte in the present experiment. Normal successive cultivation was performed using Dulbecco's modified Eagle MEM medium containing 10% calf serum (CS) at 37° C. in the presence of 5% $CO_2$. To evaluate the inhibitory effect on differentiation induction into adipocytes, the above-mentioned cells were removed from a dish by trypsin treatment to obtain cell suspension, and then after separation by centrifugation at 1,000 rpm for 3 minutes at 4° C., the concentration was adjusted to $3.5 \times 10^4$ cells/ml, and 200 µl aliquots were placed into a 96-well plate to prepare an examination plate. After 72 hours, 2 µl each of a sample dissolved in 10% DMSO was placed into each of the examination plate wells. Simultaneously, dexamethasone and isobutylmethyl xanthine were added to a final concentration of 20 µM and 10 mM, respectively. After 48 hours, the media was removed, 200 µl of fresh media was added, and the same concentration of sample was added again.

Furthermore, insulin was added to a final concentration of 17 μM. Subsequently, media exchange and addition of accompanying reagents and insulin were carried out at 3-day intervals. 8 to 10 days later, media were removed, cells were washed with PBS(−), immobilized using 10% formalin solution, adipose granules stored in the cells were stained with Oil Red-O/60% isopropanol saturated solution for 1 hour at room temperature. After staining, excess Oil Red O solution was removed using PBS(−). Observation of the stained adipose granules under a light microscope confirmed that the cells had undergone differentiation induction.

In a system for evaluating the inhibitory activity against adipocyte differentiation induced by insulin addition, acetic acid ($^{14}C-CH_3COOH$) incorporation activity, which is used as an index for differentiation induction activity, and incorporation activity of glucose ($^{14}C$-2-deoxyglucose), which is known not to be metabolized in cells, were used as indices.

Figure 1:
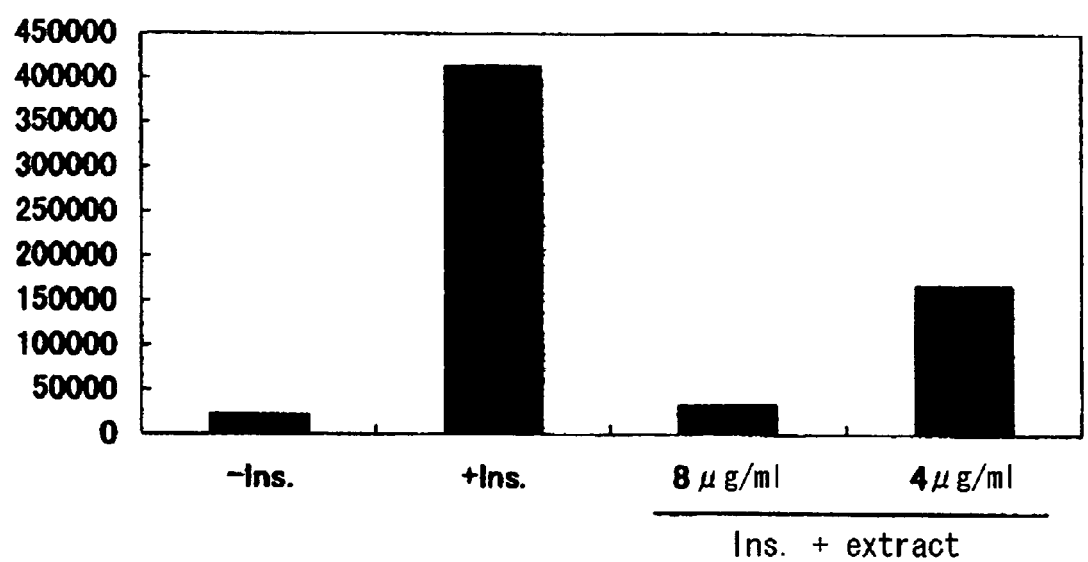
FIG. 1 is a diagram showing the inhibitory effect of *Calea* extract on adipocyte differentiation induction. The ordinate shows $^{14}C$—$CH_3COOH$ incorporation (cpm). "−Ins.", "+Ins.", and "Ins.+" on the abscissa indicate no addition of insulin, addition of insulin, and addition of both insulin and *Calea* extract to the sample, respectively.

In the system where acetic acid incorporation activity was used as an index, first the cells were placed into a 24-well plate at a density of $4.2 \times 10^4$ cell/well. After 72 hours, *Calea* extract solution, IBMX (10 mM), and dexamethazone (20 μM) were added, and was cultivated for another 48 hours. Then, the media was exchanged to a fresh media, and *Calea* extract solution and insulin (17 μM) were added. The media was exchanged to a fresh media at 3-day intervals, and *Calea* extract solution and insulin were added each time. After 9 days of cultivation following insulin addition, $_{14}C$-sodium acetate was added to a concentration of 1 μCi/ml, and was cultivated for 3 hours. Then, the media was removed, the cells were washed twice using 2 ml of PBS(−) and then dried for a few minutes on a clean bench. Next 1 ml isopropanol was gently added, left standing for a few minutes, and then isopropanol was collected and transferred to a scintillation vial. Isopropanol extraction was performed 2 more times. Using a liquid scintillation counter, radioactivity of the isopropanol fraction (adipose component) was measured. Next, upon completely drying the isopropanol extracted cells, the cells were dissolved using 200 μl of 0.1 N NaOH, and then were neutralized with 200 μl of 1 M Tris-HCl pH7.5. Then, protein quantification was performed according to the Bradford dye-binding method. For the adipose synthesis activity, $^{14}C-CH_3COOH$ incorporation activity per amount of protein was used as an index. Upon analysis, approximately 50% and nearly 100% incorporation inhibitory activities were indicated at concentrations of 4 μg/ml and 8 μg/ml extract solutions, respectively (FIG. 1).

Figure 2:
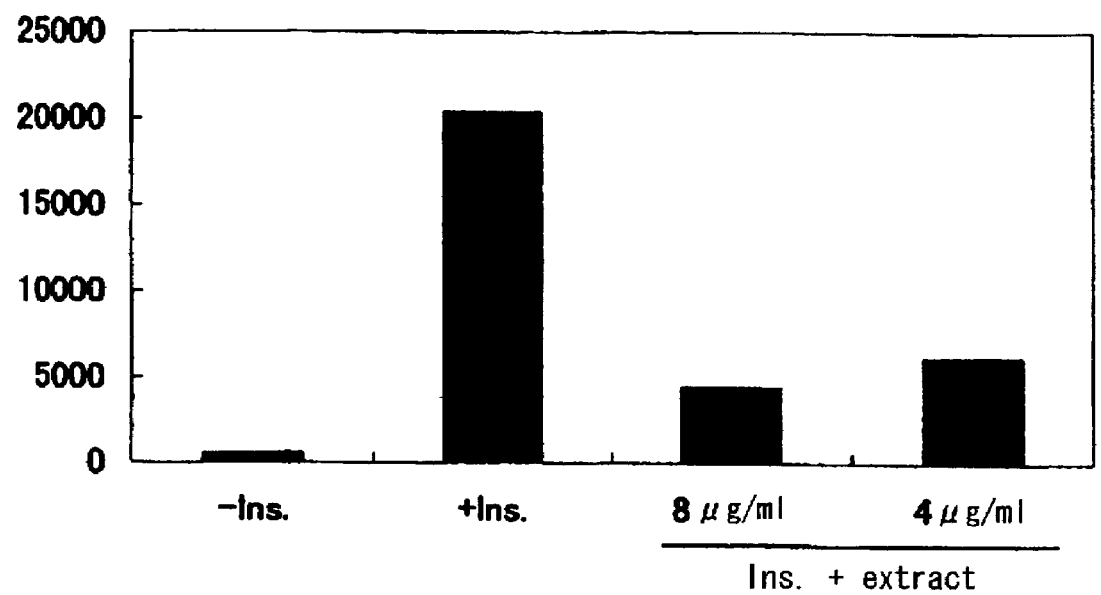
FIG. 2 is a diagram showing the inhibitory effect of *Calea* extract on adipocyte differentiation induction. The ordinate shows $^{14}C$-2-deoxyglucose incorporation (cpm). "−Ins.", "+Ins.", and "Ins.+" on the abscissa indicate no addition of insulin, addition of insulin, and addition of both insulin and *Calea* extract to the sample, respectively.

On the other hand, in a system wherein glucose incorporation activity is used as an index, cells were placed into a 24-well plate at a density of $4.2 \times 10^4$ cells/well. After 72 hours, *Calea* extract solution, IBMX (10 mM), and dexamethazone (20 μM) were added, and cells were cultivated for another 48 hours. Then, the media was exchanged to a fresh media, and *Calea* extract solution and insulin (17 μM) were added. The media was exchanged to a fresh media at 3-day intervals, and *Calea* extract solution and insulin were added each time. After 9 days of cultivation after insulin addition, the media was replaced with 500 μl/well of glucose deficient DMEM media, and was cultivated for 15 minutes. Then, $^{14}C$-2-deoxyglucose (Amersham Pharmacia Biotech) was added to a final concentration of 0.25 μCi/ml, and was cultivated for 15 minutes. Then, the cells were washed three times with ice cold PBS(−) containing 10 mM glucose, were removed from the dish using trypsin, and were transferred to a scintillation vial. Using a liquid scintillation counter, radioactivity of $^{14}C$-2-deoxyglucose incorporated into the cells was measured. Upon analysis, approximately 25% and approximately 15% of incorporation inhibitory activities were indicated at extract solution concentrations of 4 μg/ml and 8 μg/ml, respectively (FIG. 2).

EXAMPLE 2

Identification of Compounds Having Adipocyte Differentiation Induction Inhibitory Activity in *Calea* Extract Solution From Example 1, a compound existing in the *Calea* extract solution was thought to inhibit differentiation induction of adipocytes. Consequently, compounds having adipocyte differentiation induction inhibitory activity were identified.

Figure 3:
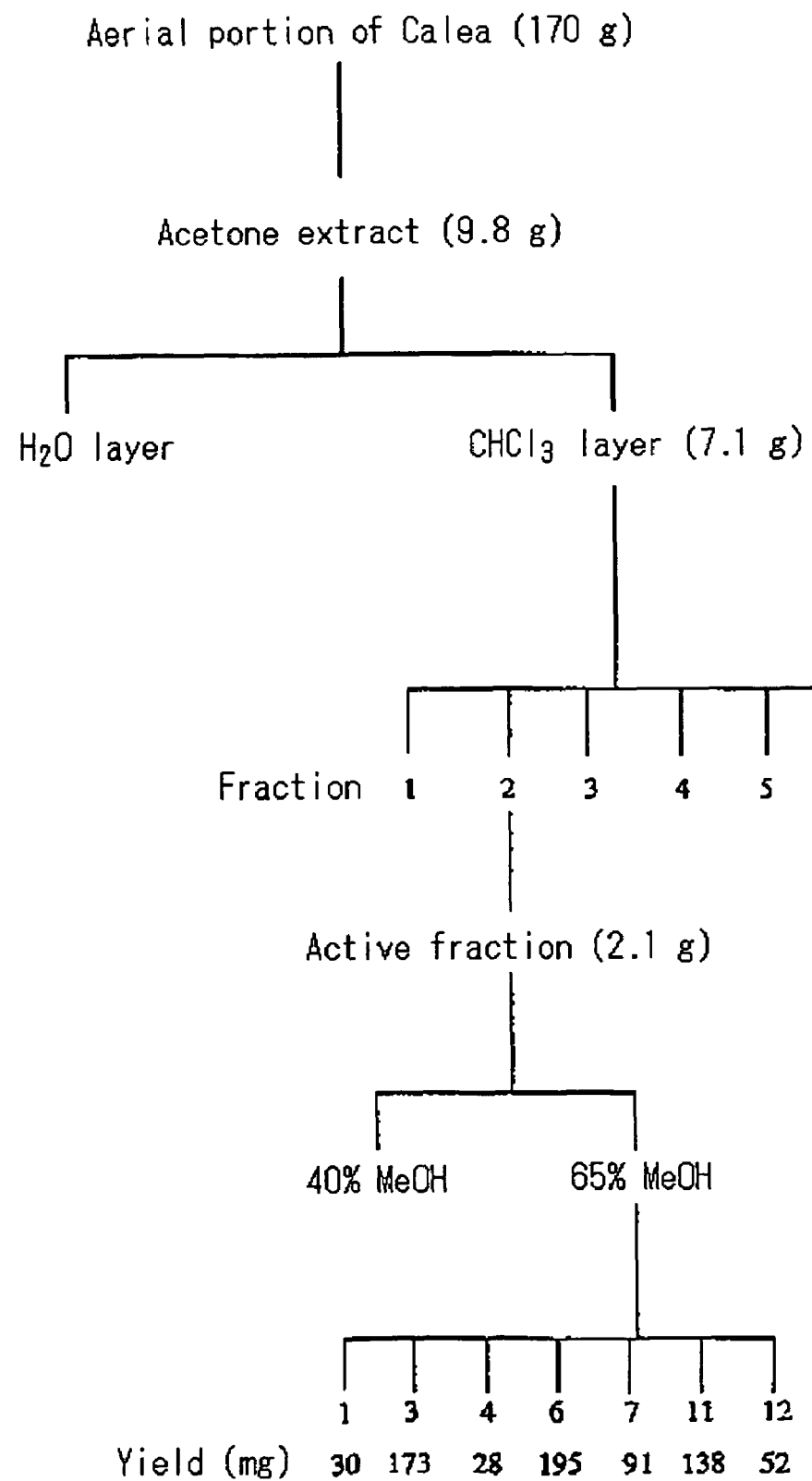
FIG. 3 is a diagram showing the isolation process of compounds (sesquiterpenoid derivatives) having an inhibitory effect on adipocyte differentiation induction.

Specifically, first, the above-mentioned compound was isolated by the process indicated in FIG. 3. The aerial portion of *Calea* (170 g) was ground, and was extracted by heated reflux (24 hours×2 times) using acetone. After concentrating the extracted solution under reduced pressure (9.8 g), the solution was distributed into chloroform and water. Upon concentrating the chloroform fraction under reduced pressure (7.1 g), the concentrated extract was dissolved in $CHCl_3$, and was chromatographed through a silica gel column (50×200 mm: 400 ml). Practically, 1200 ml each of solvents composed of $CHCl_3$:MeOH=30:1and 20:1were used for elution in order. 6fractions, each containing 400 ml, were obtained. Active fraction 2 was concentrated under reduced pressure (2.1 g). Next, the concentrated extract of the active fraction was dissolved in 5 ml of MeOH, and was chromatographed on a reverse-phase silica gel column (38× 130 mm: 150 ml Cosmosil 140C18-OPEN (Nakarai)). Specifically, the sample was added to a column material equilibrated with 40% MeOH, and was eluted using 40 and 65% MeOH in order. The active fraction eluted with 65% MeOH was concentrated under reduced pressure, and 1.14 g of active extract was obtained. Furthermore, using reverse-phase HPLC, the active ingredient was separated. Upon analysis, 7 compounds having adipocyte differentiation induction inhibitory activity were isolated under the following conditions: column, Mightysil RP-18 20×250 mm; column temperature, 40° C.; flow rate, 11.342 ml/minute; detector, 210 nm; solvent, 42% $CH_3CN$. Following the concentration under reduced pressure, each compound was recrystallized from $Et_2O$. The retention times of the isolated compounds were, compound 1: 13.5 minutes; compound 3: 18.1 minutes; compound 4: 20.2 minutes; compound 6: 23.3 minutes; compound 7: 25.3 minutes; compound 11: 35.1 minutes; and compound 12: 38.3 minutes.

Next, to identify the above-mentioned compounds, their physico chemical properties were investigated (Table 1).

TABLE 1

|  | 1 | 3 | 4 + 5 | 6 | 7 | 11 | 12 |
|---|---|---|---|---|---|---|---|
| m.p. (° C.) | 142-144 | 133-135 | 170-172 | 150-153 | 99-101 | decomp. | 98-100 |
| EI/MS |  |  | 406 | 406 |  | 450 | 432 | 434 |
| cation FAB/MS | 433 |  |  | 449 |  |  |  |
| $[\alpha]_0^{25}$ (c 0.001, $CHCl_3$) | 184.2 | 192.2 | 92.1 | 154 | 168.7 | — | 195.4 |

Furthermore, by ¹H (Table 2, Table 3) and ¹³C-NMR analysis (Table 4), as well as various two-dimensional NMR, relative configuration of each compound was determined and respective structural formula was determined. As a result, all of these compounds having the inhibitory activity on the induction of adipocyte differentiation were revealed to be sesquiterpenoid derivatives. In particular, compounds 1, 4, 7, and 12 were novel sesquiterpenoid derivatives.

TABLE 2

|  | 1 | 3 | 4 | 6 | 7 |
|---|---|---|---|---|---|
| 2 | 4.21(d, 4.1Hz, 1H) | 6.50(d, 12.0, 1H) | 3.08(dd, 16.0, 8.0Hz, 1H)<br>3.60(dd, 16.0, 9.5Hz, 1H) | 4.30(d, 4.4Hz, 1H) | 4.27(d, 4.1Hz, 1H) |
| 3 | 3.30(dd, 9.4, 4.3Hz, 1H) | 5.98(dd, 12.0 and 12.0, 1H) | 5.92(m, 1H) | 3.34(dd, 9.4, 4.3Hz, 1H) | 3.35(dd, 9.4, 4.1Hz, 1H) |
| 4 | 1.45:assigned from H—H COSY | 3.05(m, 1H) |  | 1.45:assigned from H—H COSY | 1.45:assigned from H—H COSY |
| 5 | 1.46, 1.90(each m, 1H) | 1.38(m, 1H)<br>1.80(m, 1H) | 2.77(dd, 15.0, 4.0Hz, 1H)<br>2.86(dd, 15.0, 3.6Hz, 1H) | 1.50, 1.96(each m, 1H) | 1.51, 1.95(each m, 1H) |
| 6 | 4.80(dd, 12.2, 4.5Hz, 1H) | 4.55(dd, 11.7, 4.9Hz, 1H) | 4.95(m, 1H) | 4.84(dd, 12.1, 4.5Hz, 1H) | 4.86(dd, 12.1, 4.3Hz, 1H) |
| 7 | 2.34(br s, 1H) | 2.60(s, 1H) | 2.68(m, 1H) | 2.38(br s, 1H) | 2.39(br s, 1H) |
| 8 | 5.66(dd, 10, 1.7Hz, 1H) | 5.55(s, 1H) | 5.90(dd, 10.5, 1.5Hz, 1H) | 5.75(dd, 9.7, 2.0Hz, 1H) | 5.72(dd, 9.9, 1.7Hz, 1H) |
| 9 | 5.73(d, 10Hz, 1H) | 5.55(s, 1H) | 5.70(d, 8.1Hz, 1H) | 5.85(d, 12.0Hz, 1H) | 5.82(d, 9.9Hz, 1H) |
| 13 | 5.81, 6.31(each m, 1H) | 5.80, 6.25(each d, 1.1, 1H) | 5.72(s, 1H)<br>6.30(d, 3.4Hz, 1H) | 5.84, 6.34(each s, 1H) | 5.85(d, 1.0Hz, 1H)<br>6.34(s, 1H) |
| 14 | 1.19(d, 7.1Hz, 3H) | 1.05(d, 6.3, 3H) | 1.86(s, 3H) | 1.23(d, 6.1Hz, 3H) | 1.21(d, 6.1Hz, 3H) |
| 15 | 1.45(s, 3H) | 1.30(s, 3H) | 1.35(s, 3H) | 1.46(s, 3H) |  |
| Acetyl |  |  |  |  |  |
| 2' |  | 1.95(s, 3H) |  |  |  |
| Meacr |  |  |  |  |  |
| 3' | 5.56, 6.03(each m, 1H) | 5.45, 5.95(each s, 1H) | 5.60, 6.00(each m, 1H) | 5.51(m, 1H)<br>5.97(s, 1H) | 5.58(m, 1H)<br>6.05(s, 1H) |
| 4' | 1.83(br s, 3H) | 1.78(s, 3H) | 1.87(s, 3H) | 1.78(s, 3H) | 1.83(s, 3H) |
| Acetyl |  |  |  |  |  |
| 2" | 2.03(s, 3H) |  | 2.06(s, 3H) |  |  |
| Meacr |  |  |  |  |  |
| 3" |  |  |  | 5.66(m, 1H)<br>6.16(s, 1H) |  |
| 4" |  |  |  | 1.90(s, 3H) |  |
| iBu |  |  |  |  |  |
| 2"' |  |  |  |  | 2.57(dq, 7.1, 7.1Hz, 1H) |
| 3"' |  |  |  |  | 1.10(d, 7.1Hz, 3H) |
| 4"' |  |  |  |  | 1.16(d, 7.1Hz, 3H) |
| 10-OH | 3.89(br s, 1H) |  | 4.28(br s, 1H) |  | 4.05(br s, 1H) |

TABLE 3

| 11 | 12 | 12 in d 6-benzene |
|---|---|---|
| 6.03(dd, 12.0, 11.5Hz, 1H) | 5.95(dd, 12.0, 11.5Hz, 1H) | 4.95(dd, 11.8, 11.5Hz, 1H) |
| 6.64(d, 12.0Hz, 1H) | 6.54(d, 12.0Hz, 1H) | 6.02(d, 11.8Hz, 1H) |
| 3.13(m, 1H) | 3.06(m, 1H) | 2.80(m, 1H) |
| 1.45, 1.83(each m, 1H) | 1.38, 1.79(each m, 1H) | 0.95, 1.25(each m, 1H) |
| 4.63(dd, 12.0, 4.9Hz, 1H) | 4.55(dd, 11.7, 4.5Hz, 1H) | 4.38(dd, 11.7, 4.9Hz, 1H) |
| 2.66(s, 1H) | 2.56(s, 1H) | 2.48(br s, 1H) |
| 5.69(s, 1H) | 5.58(s, 1H) | 6.00(dd, 9.8, 2.1Hz, 1H)) |
| 5.69(s, 1H) | 5.58(s, 1H) | 5.73(d, 9.8Hz, 1H) |
| 5.84(d, 1.2Hz, 1H) | 5.76(d, 1.2Hz, 1H) | 5.25(d, 1.5Hz, 1H) |
| 6.33(s, 1H) | 6.25(br s, 1H) | 6.18(d, 1.0Hz, 1H) |
| 1.15(d, 6.3Hz, 3H) | 1.08(d, 7.1Hz, 3H) | 0.58(d, 6.3Hz, 3H) |
| 1.34(s, 3H) | 1.25(s, 3H) | 1.09(s, 3H) |
| 5.61(br s, 1H) | 5.47(br s, 1H) | 5.19(m, 1H) |
| 6.13(s, 1H) | 5.95(s, 1H) | 6.23(br s, 1H) |
| 1.88(s, 3H) | 1.74(s, 3H) | 1.83(br s, 3H) |
| 5.48(br s, 1H) |  |  |
| 5.94(s, 1H) |  |  |
| 1.76(s, 3H) |  |  |
|  | 2.46(dq, 7.1, 7.1Hz, 1H) | 2.34(dq, 7.1, 7.1Hz, 1H) |
|  | 1.01(d, 7.1Hz, 3H) | 0.98(d, 7.1Hz, 3H) |
|  | 1.08(d, 7.1Hz, 3H) | 0.98(d, 7.1Hz, 3H) |
| 4.13(br s, 1H) | 4.04(br s, 1H) |  |

TABLE 4

| | 1 | 3 | 4 | 6 | 7 | 11 | 12 | 12 in d6-benzene |
|---|---|---|---|---|---|---|---|---|
| C-1 | 206.0 | 204.7 | 210.7 | 206.1 | 206.0 | 204.9 | 205.1 | 204.9 |
| 2 | 55.6 | 125.3 | 36.0 | 55.7 | 55.7 | 148.1 | 148.4 | 148.2 |
| 3 | 62.8 | 148.2 | 121.5 | 62.8 | 62.7 | 125.4 | 125.7 | 125.5 |
| 4 | 26.0 | 28.3 | 136.6 | 26.0 | 25.9 | 28.3 | 28.6 | 28.3 |
| 5 | 38.8 | 40.2 | 35.9 | 38.8 | 38.7 | 40.3 | 40.6 | 40.5 |
| 6 | 74.6 | 76.3 | 76.6 | 74.7 | 74.7 | 76.4 | 76.4 | 76.2 |
| 7 | 40.9 | 41.2 | 42.0 | 40.9 | 40.9 | 41.2 | 41.7 | 41.9 |
| 8 | 73.9 | 74.4 | 67.0 | 73.8 | 73.8 | 74.3 | 74.3 | 75.1 |
| 9 | 71.5 | 73.8 | 72.5 | 71.7 | 70.8 | 74.0 | 73.2 | 73.9 |
| 10 | 79.7 | 79.2 | 80.3 | 79.9 | 79.8 | 79.4 | 79.7 | 79.8 |
| 11 | 134.3 | 134.5 | 134.1 | 134.3 | 134.2 | 134.6 | 134.9 | 135.6 |
| 12 | 168.3 | 168.7 | 168.1 | 168.4 | 168.0 | 168.8 | 169.1 | 168.6 |
| 13 | 126.8 | 126.6 | 124.4 | 126.7 | 126.8 | 126.5 | 127.0 | 126.0 |
| 14 | 18.6 | 19.7 | 25.4 | 18.6 | 18.5 | 19.7 | 20.0 | 19.6 |
| 15 | 24.5 | 23.4 | 22.3 | 24.6 | 24.4 | 23.6 | 23.9 | 23.8 |
| 1' | 165.2 | 170.3 | 165.2 | 165.4 | 165.0 | 166.6 | 165.6 | 165.8 |
| 2' | 134.8 | 20.3 | 135.1 | 134.8 | 134.8 | 134.7 | 135.2 | 135.9 |
| 3' | 127.3 | | 126.9 | 127.0 | 127.3 | 127.8 | 127.6 | 127.4 |
| 4' | 18.1 | | 18.1 | 18.0 | 18.0 | 18.0 | 18.4 | 18.4 |
| 1" | 170.4 | 165.3 | 170.4 | 166.7 | 176.0 | 165.4 | 176.8 | 176.6 |
| 2" | 20.2 | 134.9 | 20.4 | 134.5 | 33.9 | 134.9 | 34.3 | 34.4 |
| 3" | | 127.1 | | 128.2 | 18.6 | 126.9 | 19.0 | 19.0 |
| 4" | | 18.0 | | 18.0 | 18.8 | 18.1 | 19.3 | 19.3 |

EXAMPLE 3

Figure 4:
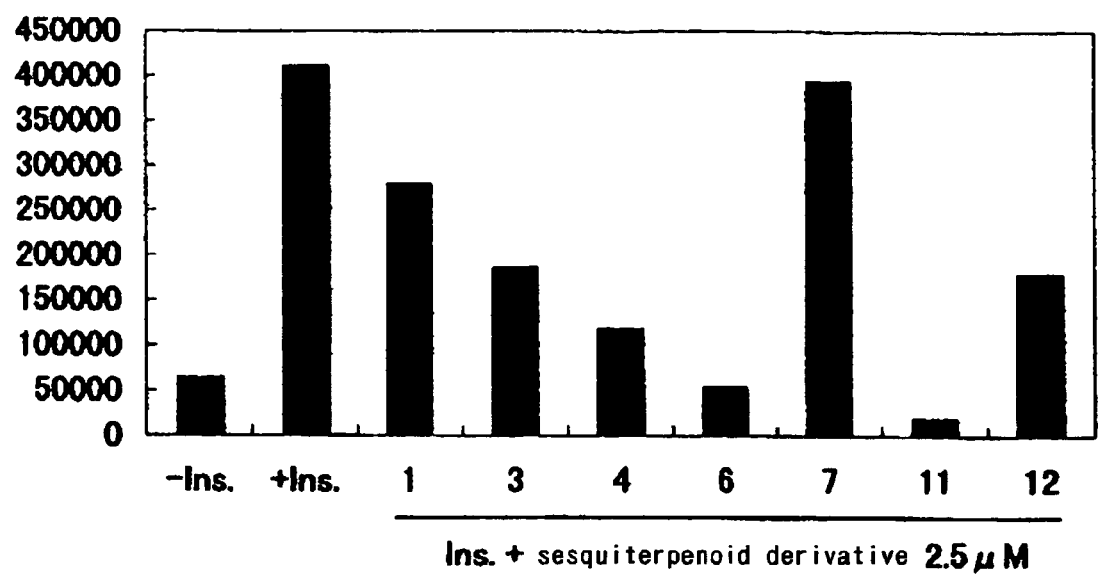
FIG. 4 is a diagram showing the inhibitory effect of sesquiterpenoid derivatives on adipocyte differentiation induction. The ordinate shows $^{14}C$—$CH_3COOH$ incorporation (cpm/mg protein) "−Ins.", and "+Ins." on the abscissa indicate no addition of insulin, and addition of insulin to the sample, respectively. 1, 3, 4, 6, 7, 11, and 12 on the abscissa indicate samples to which compounds 1, 3, 4, 6, 7, 11, and 12, respectively, have been added in combination with insulin.

Examination of the Relationship Between Structure and Activity of *Calea* Extract Structure-activity relationships of the 7 compounds obtained in Example 2 were examined. Inhibitory activities of respective compounds on the differentiation induction of 3T3-L1 cells into adipocytes were compared in the system described in Example 1 that uses acetic acid incorporation activity as the index. As a result, high incorporation inhibitory activity was confirmed for compounds 11 and 6. Ranking the compounds in the order of higher inhibitory activity, the order was: compound 11>6>4>3=12>1>7 (FIG. 4).

Industrial Applicability

The present invention provides sesquiterpenoid derivatives having adipocyte differentiation inhibitory effect. Furthermore, the present invention provides pharmaceutical compositions and food compositions for prevention, improvement, or treatment of obesity or obesity related diseases that contain *Calea* extract or the sesquiterpenoid derivative as an active ingredient. The use of these compositions presents great expectations for effective prevention, improvement, or treatment of obesity or obesity related diseases.

The invention claimed is:

1. An isolated sesquiterpenoid compound having any one of the following structural formulae:

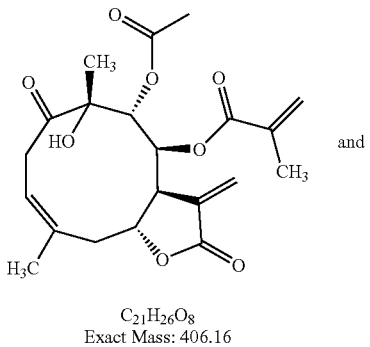

(1) compound 4

$C_{21}H_{26}O_8$
Exact Mass: 406.16
Mol. Wt.: 406.43
C, 62.06; H, 6.45; O, 31.49

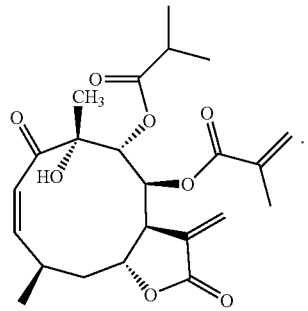

(2) compound 12

$C_{23}H_{30}O_8$
Exact Mass: 434.19
Mol. Wt.: 434.48
C, 63.58; H, 6.96; O, 29.46

2. An adipocyte differentiation inhibitor comprising as an active ingredient the sesquiterpenoid compound set forth in claim 1, wherein said sesquiterpenoid compound has an inhibitory effect on adipocyte differentiation.

3. A pharmaceutical composition, comprising a pharmaceutical carrier and, as an active ingredient, an isolated sesquiterpenoid compound wherein said sesquiterpenoid compound has an inhibitory effect on adipocyte differentiation, and wherein the sesquiterpenoid compound has any one of the following structural formulae:

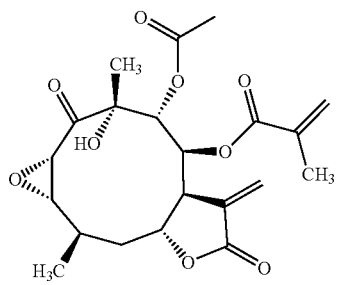

(1) compound 1

$C_{21}H_{26}O_9$
Exact Mass: 422.16
Mol. Wt.: 422.43
C, 59.71; H, 6.20; O, 34.09

-continued (2) compound 4

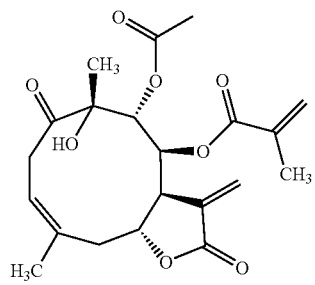

C$_{21}$H$_{26}$O$_8$
Exact Mass: 406.16
Mol. Wt.: 406.43
C, 62.06; H, 6.45; O, 31.49 and (3) compound 12

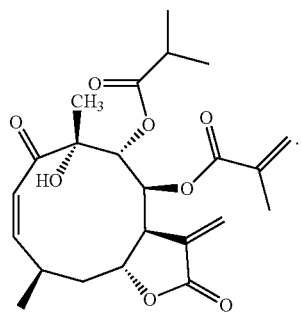

C$_{23}$H$_{30}$O$_8$
Exact Mass: 434.19
Mol. Wt.: 434.48
C, 63.58; H, 6.96; O, 29.46

4. A food composition, comprising as an active ingredient an isolated sesquiterpenoid compound wherein said sesquiterpenoid compound has an inhibitory effect on adipocyte differentiation, and wherein the sesquiterpenoid compound has any one of the following structural formulae:

(1) compound 1

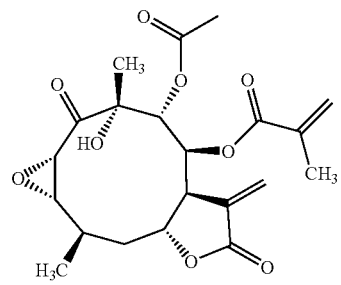

C$_{21}$H$_{26}$O$_9$
Exact Mass: 422.16
Mol. Wt.: 422.43
C, 59.71; H, 6.20; O, 34.09

(2) compound 4

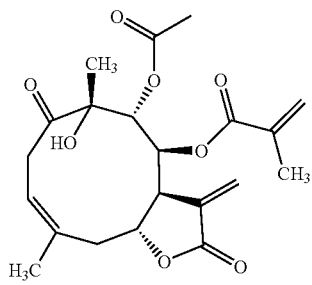

and

C$_{21}$H$_{26}$O$_8$
Exact Mass: 406.16
Mol. Wt.: 406.43
C, 62.06; H, 6.45; O, 31.49

(3) compound 12

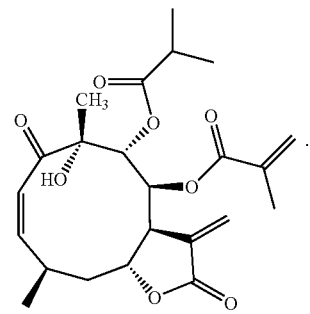

C$_{23}$H$_{30}$O$_8$
Exact Mass: 434.19
Mol. Wt.: 434.48
C, 63.58; H, 6.96; O, 29.46

* * * * *

UNITED STATES PATENT AND TRADEMARK OFFICE
CERTIFICATE OF CORRECTION

PATENT NO.        : 7,387,800 B2
APPLICATION NO.   : 10/485801
DATED             : June 17, 2008
INVENTOR(S)       : Munekazu Iinuma et al.

It is certified that error appears in the above-identified patent and that said Letters Patent is hereby corrected as shown below:

On the Title Page,
Item 75, lines 5-6, "Hiroto Suzuki, Toyama" should read --Hiroto Suzuki, Tokyo--.

Column 11,
Lines 27-28, "$_{14}$C-sodium" should read --$^{14}$C-sodium--.

Signed and Sealed this

Second Day of September, 2008

JON W. DUDAS
*Director of the United States Patent and Trademark Office*

UNITED STATES PATENT AND TRADEMARK OFFICE
CERTIFICATE OF CORRECTION

PATENT NO. : 7,387,800 B2
APPLICATION NO. : 10/485801
DATED : June 17, 2008
INVENTOR(S) : Munekazu Iinuma et al.

It is certified that error appears in the above-identified patent and that said Letters Patent is hereby corrected as shown below:

Column 11,
Lines 27-28, "$_{14}$C-sodium" should read --$^{14}$C-sodium--.

Signed and Sealed this

Ninth Day of September, 2008

JON W. DUDAS
*Director of the United States Patent and Trademark Office*